United States Patent [19]

Karmen

[11] Patent Number: 5,591,644

[45] Date of Patent: Jan. 7, 1997

[54] SENSITIVE ON LINE ASSAY OF CHROMATOGRAPHIC EFFLUENT

[75] Inventor: Arthur Karmen, Manhasset, N.Y.

[73] Assignee: Albert Einstein College of Medicine of Yeshiva University, Bronx, N.Y.

[21] Appl. No.: 241,662

[22] Filed: May 11, 1994

Related U.S. Application Data

[63] Continuation of Ser. No. 552,147, May 11, 1990, abandoned.

[51] Int. Cl.$^6$ ............................................... G01N 35/08
[52] U.S. Cl. .................... 436/53; 422/52; 422/53; 422/66; 422/67; 435/287.3; 435/288.6; 435/288.7; 436/46; 436/47; 436/164; 436/172
[58] Field of Search ............................ 422/66, 67, 102, 422/52, 53, 65, 104, 91, 70, 63; 250/227; 356/244; 435/805, 300, 308, 808, 287.3, 288.6, 288.7; 436/23, 53, 50, 47, 46, 57, 164, 172

[56] References Cited

U.S. PATENT DOCUMENTS

| | | | |
|---|---|---|---|
| 3,010,800 | 11/1961 | Whitehead et al. | 422/82 |
| 4,158,545 | 6/1979 | Yamashita et al. | 436/50 |
| 4,253,846 | 3/1981 | Smythe et al. | 436/53 |
| 4,257,862 | 3/1981 | Schnipelsky et al. | 422/63 |
| 4,349,510 | 9/1982 | Kolehmainen et al. | 422/66 |
| 4,552,723 | 11/1985 | Adams et al. | 422/66 |
| 4,649,124 | 3/1987 | Hall | 422/89 |
| 4,689,202 | 8/1987 | Khoja et al. | 436/47 |
| 4,740,298 | 4/1988 | Andresen et al. | 422/66 |
| 4,781,891 | 11/1988 | Galle et al. | 422/63 |
| 4,855,601 | 8/1989 | Savoyet | 422/66 |
| 4,980,130 | 12/1990 | Metzger et al. | 422/67 |

OTHER PUBLICATIONS

A. Karmen, G. Malikin and S. Lam, J. *Chromatogr.* 302 (1984) 31.

A. Karmen, G. Malikin, L. Freundlich and S. Lam, J. *Chromatogr.* 349 (1985) 27.

D. C. Fenimore and C. M. Davis, *Anal. Chem.*, 53 (1981) 252A.

S. Baba, Y. Suzuki, Y. Sasaki and M. Horie, *J. Chromatogr.*, 392 (1987) 157.

S. Baba, M. Horie and K. Watanabe, *J. Chromatogr.* 244 (1982) 57.

*Primary Examiner*—Jill Warden
*Assistant Examiner*—Jan M. Ludlow
*Attorney, Agent, or Firm*—Amster, Rothstein & Ebenstein

[57] ABSTRACT

A method for on-line assay in column chromatography of a property that requires appreciable time for sensitive measurement has the steps of separating the effluent into discrete fractions at equal time intervals, sequentially passing each fraction through each of a series of detectors, while preventing each fraction from mixing with another; and, for each fraction, calculating the assay from the information provided by each detector during the time interval the fraction passed through it.

30 Claims, 2 Drawing Sheets

SENSITIVE ON LINE ASSAY OF CHROMATOGRAPHIC EFFLUENT

This is a continuation of application(s) Ser. No. 07/552,147 filed on May 11, 1990, now abandoned.

BACKGROUND OF THE INVENTION

The present invention relates to the on-line detection of properties of the effluent of column chromatography that require appreciable time for measurement, and more particularly to an assay of radioactivity with enhanced sensitivity and resolution.

In column chromatography, such as gas-liquid, gas-solid, liquid-liquid or liquid-solid chromatography, detection is generally accomplished by passing the column effluent through or past a detector which senses and records over time the rises and falls of a property of the effluent related to the concentration of the compounds of interest. Both identification and quantification of components of the mixture being separated depend on accurate recording of these concentration changes and the time at which they occur. In order to achieve and preserve maximal resolution, detector volumes are generally minimized and flow rates are adjusted for maximal response to rapid changes in concentration. Only small portions of the effluent are present in the detector at any given time, and the time each portion remains in the detector is minimized.

When radioactivity is to be measured, however, maximizing resolution limits sensitivity. Because of the random nature of radioactive decay, the precision of any radioassay is a function of the number of radioactive events that contribute to the measurement. In radiochromatography, each portion of the effluent must remain in the detector sufficiently long for the required number of radioactive emissions to be detected. Detector volumes and flow rates are compromises between these opposing requirements. In current high performance (or pressure) liquid chromatography (HPLC), for example, time in the detector can often be extended up to about 20 seconds without intolerable degradation of resolution, even though in other detectors much shorter times are generally thought desirable. If the sample contains less radioactivity than can be measured with acceptable precision in 20 sec., flow-through detection is generally not useful. The alternative is to fractionate the effluent for subsequent radioassay of each fraction for much longer times. To achieve the same resolution, separate fractions must be collected at least every 20 sec. Many fractions must then be assayed, and this can occupy a counting device for many hours. For this reason, most workers find flow-through detectors more convenient to use and reserve fraction-collecting for those assays involving very low levels of radioactivity and either limit the time each fraction is counted or sacrifice resolution for sensitivity by collecting fewer fractions.

Baba et al. described delivering a stream of HPLC effluent mixed with scintillation fluid, but without segmentation of the stream to achieve discrete fractionation, through five scintillation counters in series. S. Baba, et al., *J. Chromatograph*, 244 (1982) 57 and 392 (1987) 157. They recorded the predicted increase in precision over that from a single detector but also noted appreciable and predictable loss of resolution, manifested by an increase in peak width from the first to the fifth detector, caused by mixing of one part of the effluent with the next. This effect is particularly troublesome with detergent-containing scintillation fluids which tend to wet even polytetrafluoroethylene (PTFE) tubing.

Accordingly, it is an object of the present invention to provide a method for the on-line assay of a property of a stream which requires appreciable time for sensitive measurement, which method combines high sensitivity and high resolution.

It is also an object to provide such a method wherein the stream is a column chromatographic effluent.

Another object is to provide such a method wherein the assay is a radioassay.

A further object is to provide such a method which is simple, easy, and economical.

SUMMARY OF THE INVENTION

The present invention is a system for increasing the sensitivity of on-line radioassay of chromatographic effluent. Unlike previous methods that pass the column effluent through a radiation detector, which methods have limited sensitivity because the time in the detector must be kept short, the effluent is divided into discrete fractions, which are then each passed sequentially through an array of a number of detectors in series. The radioactive events detected in each detector during each time interval are recorded and are summed electronically to reflect the number of events generated by each fraction passing through all detectors. The resolution achieved is the same as that given by a single flow-through detector with comparable convenience. Sensitivity is much enhanced in proportion to the increased number of radioactive events detected during the increased total time of assay.

The effluent is divided into a sufficiently large number of fractions to obtain the necessary resolution. Each fraction is prevented from mixing with the next. Each fraction is then passed sequentially through or past a series of detectors in each of which each fraction spends equal time. The radioactive events detected in each detector during each time period are accumulated separately in electronic memory so that, at the completion of the process, a single memory bank contains the sum of the radioactive events detected as a fraction passed through the series of detectors. The first portion of memory, for example, contains the sum of the radioactive events detected in the first detector during the first assay period, the second detector during the second period, the third detector in the third counting period, and so forth, with the number of addends contributing to the sum given by the number of detectors used. The sum then reflects the total detected radioactivity of the first portion of the effluent. Each succeeding portion of the effluent follows the first through the detector array with the events detected summed in a succeeding memory bank.

The resolution of the assay remains defined by the number of fractions taken, while the sensitivity and precision of the assay are enhanced over the conventional measurement using a single detector in the statistically predictable manner given by the increased time of radioassay, now given by the product of the time in each detector and the number of detectors.

More generally, the present invention resides in a method for the on-line assay of a stream (e.g., a column chromatographic effluent) for a property which requires both appreciable time for sensitive measurement and no loss of resolution. The method comprises the steps of separating the stream (e.g., the effluent) into discrete fractions at equal time intervals; sequentially passing each fraction through each of a series of detectors for the same interval, while preventing each fraction from mixing with another; and, for each fraction, calculating the assay from the information provided by each detector during the time interval the fraction passed through it.

In a preferred embodiment of the present invention, the assay is a radioassay, the property being measured is radioactivity, and the detectors detect radioactivity. The detectors may detect the radioactivity on a rapidly-reading radiation detector — e.g. by ionization, Geiger or proportional counters (which depend on the effect of radiation in causing ionization in gases) or by liquid or solid scintillation counters (which depend on the effect of radiation in causing the excitement of luminescence) or solid state detectors. The effluent is typically a liquid or gas column chromatographic effluent, preferably a high performance liquid chromatographic (HPLC) effluent. The fractions are taken from the effluent at intervals of 20 sec. or less, collected in pockets formed on an elongate strip of fluorocarbon film moved stepwise past the source of effluent. The solvents in each fraction collected in a pocket are evaporated to produce a condensed dry fraction prior to passage of the dry fraction through the first detector in the series. Where the effluent is a gas column chromatographic effluent, each fraction is stripped into a stream of solvent prior to collection.

Preferably the effluent is fractionated by dividing it at predetermined time intervals into a plurality of fractions which are prevented from subsequently mixing with each other, and each fraction is sequentially passed through each detector for an equal time interval, preferably equal to the predetermined time interval.

BRIEF DESCRIPTION OF THE DRAWING

The above brief description as well as further objects and features of the present invention will be more fully understood by reference to the following detailed description of the presently preferred, albeit illustrative, embodiments of the present invention when taken in conjunction with the accompanying drawing wherein.

DETAILED DESCRIPTION OF THE PREFERRED EMBODIMENTS

The principles of the present invention will be set forth here in terms of an on-line radioassay of a high performance (or high pressure) liquid chromatographic (HPLC) effluent. Thus the property to be measured is radioactivity, and the detectors directly or indirectly detect radioactive events. It will be appreciated, however, that the principles of the present invention are broadly applicable to an on-line assay of any property of any stream (typically a column chromatographic effluent) that requires appreciable time for sensitive measurement, more time than can be allowed for any portion of the stream to remain in a single detector without sacrificing resolution.

In each instance, the three steps of the method are the same: fractionation, detection, and data reduction. Each of these steps will be separately described hereinbelow.
Fractionation The column effluent is divided into a large number of equal fractions, each of which is prevented from mixing with subsequent and previous samples by well known fractionating techniques. A variety of techniques for fractionation of a fluid stream are well known in the art. See, for example, U.S. Pat. Nos. 4,121,466 and 4,253,846. For example, the solvent of a fraction may be evaporated leaving a solid fraction, the fractions may be adsorbed or deposited as distinct fractions on a solid matrix, or an effluent stream delivered to non-wetting tubing and distinct fractions created therein by segmenting the stream of effluent with immiscible fluid.

As an example of the process of the present invention, the liquid effluent of an HPLC column was fractionated using a collector based on the fluorocarbon film technology used to concentrate samples and to apply them to thin-layer chromatography (TLC) plates by Fenimore and Davis, and adapted as a fraction collector for HPLC subsequently by Karmen et al. D.C. Fenimore et al., *Anal. Chem.*, 53 (1981) 252A; A. Karmen et al., *J. Chromatography*, 302 (1984) 31 and 349 (1985) 267. A hollow rectangular aluminum plate was constructed using two 1/8 inch thick aluminum strips, 1 inch wide and 48 inches long, separated by a gasket formed of 1 mm thick, 8 mm wide silicone rubber at the perimeter that defines a central cavity. The top surface contains a row of 80 hemispherical wells, 0.9 mm deep, 8 mm in diameter, 1 cm center-to-center, with a 1-mm hole drilled at the bottom of each well to connect it to the central cavity which was also connected with fittings for drawing a vacuum or applying a pressure. The top surface was polished to mirror finish. Fluorocarbon-coated sample wells were formed by placing a sheet of 0.025 mm thick fluorocarbon film over the plate and drawing a vacuum in the cavity which caused the film to cling to the polished surface of the wells. The column effluent was delivered to each well through 15 cm×0.002 in. ID stainless-steel capillary tube, fitted with a 2 mm long Teflon (PTFE) sleeve at the end. Equal sized portions of column effluent, each containing predetermined 20–80 ul, depending on the analysis being performed, were deposited in each pocket. After each collection period (ca 20 sec), the plate was moved 1 cm so that the next well was under the effluent tube. The wells containing the effluent were then passed through 10 stations, in each of which the solvent was removed by gentle streams of heated nitrogen, and finally passed through an array of detectors.

Clearly, other fractionation techniques may be used in place of that described above, the exact fractionation technique selected being dependent upon various factors well known to those skilled in e the art, including the aqueous or non-aqueous nature of the stream, etc. The stream is typically a liquid or gas chromatographic effluent. In a high pressure liquid chromatographic effluent, fractions of the solution are taken at nominal intervals (e.g., 20 sec.), depending on the speed of the analysis and the resolution required. The fractions are collected in a series of pockets, formed on a long strip of fluorocarbon film, which pockets are moved sequentially past the exit line of the column in a stepwise manner. The solvents in each fraction are removed by evaporation, and the resulting dry material, condensed in the center of the pocket of the non-wetting fluorocarbon film, is passed to the first detector in the series. Where the effluent is a gas chromatographic effluent, the compounds of interest are stripped from the gas stream continuously into a liquid stream, which is then fractionated as described above.

The time intervals are infinitely adjustable for different separations and different applications. The series of fractions can be collected on a belt of film moving linearly through a long string of detectors, or on a belt moving in serpentine fashion through a string of detectors arranged in serpentine fashion (e.g., 20 rows of 20 columns).
Detection An experiment was performed using as the detector a Model RS Radio TLC scanner (Radiomatic Instruments and Chemical Co., Inc., Tampa, Fla., USA). This position-sensitive proportional counter consists of a 20 -cm-long, windowless proportional counter, used with "P-10" gas, connected to a 1024-channel multichannel analyzer. With its associated aperture, it offers 1- to 2-mm resolution of $^{14}C$ thin-layer chromatography (TLC) plates. For assaying a TLC plate, the counter moves over the plate stepwise in small increments at predetermined counting intervals. When the beta-particle interacts with the gas in the counter, an electric discharge occurs in the volume where the interaction occurs. This induces a charge in an inductive delay line close to the wire. The charge travels as a pulse to the ends of this delay line at measurable speed. The position at which the event occurs is sensed electronically by the time of arrival of the pulse at each end of the delay line. For the application described here, however, the center line of the fluorocarbon film pockets containing the dry radioactive samples was placed under and aligned parallel with the detector wire and indexed one cm. every 20 sec along the length of the wire. At the end of each 20 sec interval, the counting rate was recorded and summed as described above, as though the 20 wells were 20 well-resolved spots on a TLC plate.

A second, similar experiment was performed using as the detector a Vanguard Model 2001 1-D/2-D TLC plate scanner (Digital Diagnostic Corp., Hamden, Conn., USA). This scanner uses an array of ten 1×2.5 cm. windowless flow-counters, operated in the Geiger Mode with "Q-gas." The counters are fitted with metal collimators to achieve the required resolution in TLC scanning.

The two kinds of gas detectors used in these two experiments gave similar results. Each yielded defined resolution, the same resolution as flow-through detection, but with each sample counted many times as long (e.g., 10 times as long with the ten-detector array), with corresponding increases in sensitivity and precision.

It is contemplated that either one of the gas detector systems described hereinabove or an ionization counter could be used. The same approach can also be used with internal liquid or solid scintillation counters or solid-state detectors using a similar succession of detectors. Liquid scintillation detection can be performed using the fraction collection scheme described above with the modifications of adding scintillator fluid to each well and using photomultiplier tubes in lieu of the Geiger counters in the detector array. An alternative fractionation scheme is to add liquid scintillation fluid to the HPLC column effluent, deliver the effluent to a long length of Teflon tubing, fractionate the effluent by injecting sufficient volumes of an immiscible fluid (such as perfluorobenzene or other liquid fluorocarbon) at preselected time intervals (such as every 20 sec as described above). The combined stream can then be delivered, again at and for 20 sec intervals, to the flow cells of a sequence of flow-through liquid scintillation counters.

Liquid scintillation counting generally offers higher sensitivity, particularly for tritium ($^3H$), than external counting with a gas detector, because of reduced absorption of the beta particles by the sample. One notes, however, that scintillation counters using photomultipliers are currently much more expensive than gas counters, making the cost of an array of pairs of light detectors, arranged for coincidence detection, or a scintillation camera, such as is used in nuclear medicine, comparatively high.

As an alternative to the array of individual proportional counters, Geiger counters and scintillation counters described above, the detection step may utilize an array of ionization chambers, solid-state radiation detectors or the like. Indeed, various two-dimensional representations of the variable property may be obtained using isotope scintillation cameras or gas detectors consisting of arrays of wires (sometimes referred to as "spark chambers"). The counting rates are recorded for each fraction in each radiation detector, or in pre-set locations in each position-sensitive detector, during each time period. The resulting sums for each fraction represent the total of the radioactive events recorded for each fraction passing through all the detectors.

Each fraction preferably spends an equal time interval in each detector, and that time interval is preferably equal to the predetermined time interval at which the stream is divided into the fractions.

Data Reduction

As noted above, each fraction is passed sequentially through or past a series of detectors, in each of which detectors each fraction spends equal time, typically the same time period used to collect the fraction. The radioactive events detected in each detector during each time period are accumulated separately in electronic memory so that, at the completion of the process, a single memory bank contains the sum of the radioactive events detected as a fraction passed through the series of detectors. The first portion of memory, for example, contains the sum of the radioactive events detected in the first detector during the first assay period, the second detector during the second period, the third detector in the third counting period, and so forth, with the number of addends contributing to the sum given by the number of detectors used. The sum then reflects the radioactivity of the first portion of the effluent. Each succeeding portion of the effluent follows the first through the detector array, with the events detected being summed in a succeeding memory bank.

The sums may be displayed as they are being accumulated through the use of electronic memory, using a computer or a multichannel analyzer operated in a multiscaler mode, with continuous real time display. The counts for a particular fraction may be displayed as total accumulative counts, as counts per unit of time, or as counts per detector, as desired.

In a preferred embodiment the outputs of each detector during each time interval are stored separately in electronic or similar memory, and the assay of each fraction is calculated continuously by a microprocessor or the like, using a formula which takes into account the position of the fraction passing through the series of detectors. The results are continuously updated and displayed on the screen of a temporary data display device such as a cathode ray tube computer monitor. This display may be supplemented by a more permanent printout containing the record of the assay of each fraction generated as it leaves the last detector of the series. This combination of displays and records offers both the earliest possible indication of results and the maximum sensitivity and precision subsequently.

The resolution of the assay remains defined by the number of fractions taken, while the sensitivity and precision of the measurements are enhanced over the conventional measurements using a single detector in the statistically predictable manner given by the increased time of radioassay, now given by the product of the time in each detector and the number of detectors.

The increase in sensitivity achievable by passing many fractionated portions of the column effluent through a succession of detectors can be estimated directly from the increased time of counting: the counts recorded in 10 detectors, if a fraction spends 15–10 sec in front of each, would predictably be 10 times the number recorded if the sample were passed in front of a single detector of the same kind for the same time period. On the other hand, if the sensitivity of an array of 10 external gas detectors is compared with that of a single flow-through scintillation counter that accepts the same size fraction of the effluent (e.g., a 15 sec portion), a smaller improvement would be predicted. From considerations of geometry alone, and neglecting self-absorption of the beta particles in the sample or the carrier, the efficiency of external gas detectors reaches a maximum of only 50%, compared to ca 80% in internal liquid scintillation systems. A counter placed above the sample does not "see" the beta particles that are directed downward. Some improvement might be obtained by employing opposing detectors, one on each side of the carrier strip, arranging the spacing so that electric discharges in one do not affect the other. It would probably be more straightforward to use additional detectors to increase the number of steps in the array, increasing the sensitivity in direct proportion to their number, even through this would increase the time of completion of the assay.

Figure 1:
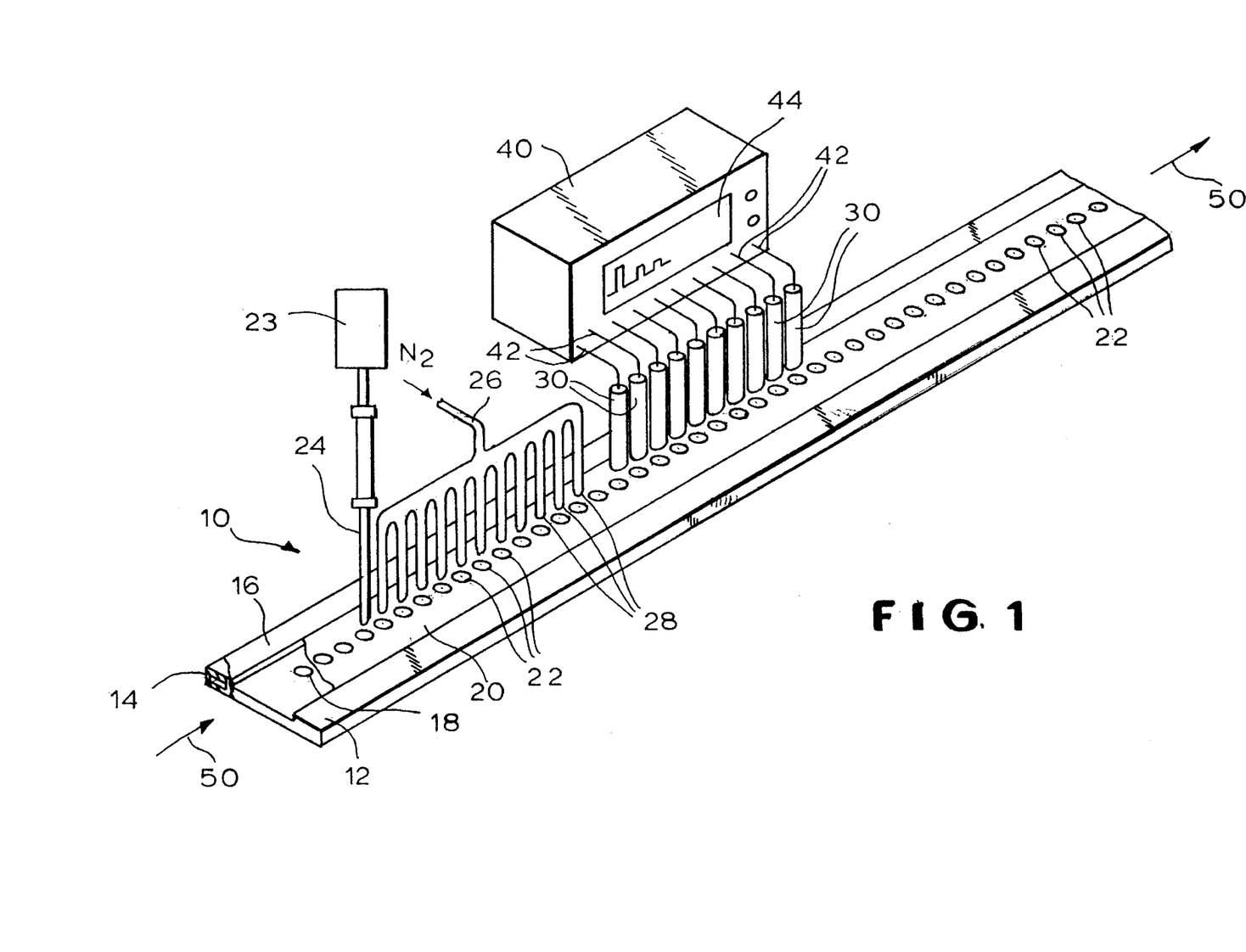
FIG. 1 is a fragmentary schematic representation of apparatus useful in the practice of the method of the present invention.

Referring now to FIG. 1, therein illustrated is apparatus, generally designated by the reference numeral 10, useful in the practice of the method of the present invention. The apparatus 10 includes a hollow aluminum plate 12 having a length of about one meter, an internal cavity 14, and a polished top surface 16. A linear series of 100 concavities 18, each about 8 millimeters in diameter, is milled into the top surface 16, each concavity 18 being connected to the plate cavity 14 by a hole about 1 millimeter in diameter. Although not illustrated, the plate cavity 14 is connected to a vacuum line, electrical strip heaters are fastened to the bottom of plate 12, and thermocouples are mounted on the plate 12 to measure its temperature. A non-wetting film 20 of polytetrafluoroethylene (PTFE) covers the plate concavities 18 to form a series of 100 pockets 22.

An HPLC column 23 has its exit line 24 depositing effluent in the fourth pocket 20 from the end. A nitrogen manifold 26 has its fingers 28 directing a stream of heated nitrogen gas to each of the next ten pockets 22 containing the sample of effluent deposited by the HPLC column exit line 24. (Obviously the nitrogen gas must be supplied in a gentle manner so as not to blow the sample out of the pocket.) An array of windowless Geiger counters 30 is provided, each counter 30 being represented in FIG. 1 as a wire mounted on the longitudinal axis of a cylinder. Not illustrated in FIG. 1 are the conventional gas inputs to each Geiger counter 30 and the gas exits adjacent the counter bottoms, facing the samples in the pockets thereunder. Each Geiger counter 30 in the array includes or is connected electrically to an individual scaler, which in turn is connected to a microprocessor or computer 40, and in particular the computer inputs 42 for multiscaling. The computer 40 includes not only a multiscaling device, but also a cathode ray tube display 44.

The hollow aluminum plate 12 (bearing the PTFE film 20, pockets 22 and the samples therein) is moved in the direction of arrows 50 by a conventional transport mechanism (not shown) such as a stepper motor which drives a chain attached to the ends of the plate 12 and passing over pulleys on each end. The transport mechanism moves the pockets 22 sequentially past the exit line 24 of the HPLC column 23 and past the array of Geiger counters 30, in the direction of the arrows 50. In FIG. 1 the position of the plate 12 relative to the HPLC column exit line 24 and Geiger counters 30 indicates that the fractionation of the chromatographic effluent is almost complete and the radioassay is approximately half complete.

While the approach of fractionating a stream into discrete fractions and passing each discrete fraction through or past a series of detectors has been described above as applied to the measurement of radioactivity, it may also be used for measuring other properties of a flowing stream. It is particularly applicable to the measurement of compounds that enter into reactions that require more than a few seconds for completion and that do not yield a stable product measurable at a later time.

An example is the detection of compounds that enter reactions that produce bioluminescence or chemiluminescence. In these reactions light is characteristically emitted for many seconds or minutes after the reagents and sample are mixed. The total light emitted is related to the number of molecules detected. The intensity of the light emitted at a fixed time after the start of the reaction, equivalent to the rate of emission of photons, can also be related to the concentration. But, when the reaction is slow, measuring the intensity over any given small time period requires a sacrifice of sensitivity. With the approach described here, the light emitted from each fraction of the stream can be measured for an extended period without sacrifice of resolution.

A second example is the measurement of a compound in a flowing stream that reacts in a biological system to produce a transient biological effect, such as the contraction or relaxation of cells in suspension, and is itself consumed in the process. The approach described here permits the effect to be observed over the entire time period of the reaction, again with no loss of resolution. The term "biologic effect" or "biological effect" as used herein refers to the effect of the substance being studied on the suspensions or other preparations of living cells, such as those of bacteria, protozoa, plants or animals — e.g., the aforementioned contraction or relaxation of cells in suspension.

The approach is also applicable to the detection of compounds by reactions that are very slow. It is the usual practice to delay the measurement, such as by passing the stream through a long tube or similar pathway to delay the time of observation. Lengthening the pathway may result in loss of resolution as one portion of the stream mixes with the next during its passage. The approach described here allows individual fractions to be observed during the entire course of their reaction. This would be helpful particularly when individual compounds react at different rates and when selection of a single time for measurement yields suboptimal results.

The approach is also applicable to the measurement of enzymes separated in chromatographic systems, particularly when different enzymes in the same mixture are present over a comparatively large range of concentrations. In these instances any single time for measurement of accumulation of product or consumption of substrate may be optimal for one but not the other concentrations. By measurement of a property related to concentration of product or substrate in different fractions continuously, the range of concentrations of enzyme that can be measured on line in a single analysis is increased.

While the method of the present invention has been described in terms of an assay of the effluent from column chromatography, clearly the method can be applied to any stream whether from a column or not — e.g., the effluent of an electrophoresis column such as a high performance capillary electrophoresis column. The method is particularly useful, however, in assays of the effluent of analytical separations.

The method of the present invention offers the convenience of virtual on-line radioactivity detection in radiochromatography, with pre-set resolution combined with the increased sensitivity obtained by using longer counting times than can be permitted with a single detector because of the requirement of preserving resolution. The on-line assay is complete only a few minutes after the analysis and is preferable to an assay which uses an off-line post-column reaction that requires several minutes for completion. Unlike other forms of on-line detection, the fractions remain available for repeated analysis off-line, when even greater sensitivity is needed.

As the count in each memory bank can be displayed continuously, the count for a fraction can be examined within a very short interval after it leaves the column. However, additional data continues to accumulate in succeeding times, increasing the precision of the assay.

There are often small differences in sensitivity or efficiency of radiation detection among apparently identical radiation detectors. As described above, the effluent stream is fractionated at predetermined time intervals, and each fraction is passed through a series of pretreatment stations for evaporation or reagent addition, preferably spending the same predetermined time interval at each station. Each fraction is then passed stepwise through the series of radiation detectors, illustrated in linear array in FIG. 1, preferably spending the same predetermined time interval at each detector. Passing each fraction through each in a series of detectors, as described above, tends to ensure that each fraction is assayed with the same efficiency or sensitivity since each sample travels the same path through the different detectors. Nevertheless, with careful control of construction and operation, different detectors can be made close to equal in performance and can be calibrated, and the data output adjusted to provide equal efficiencies. When this is done, an alternate approach is possible.

Figure 2:
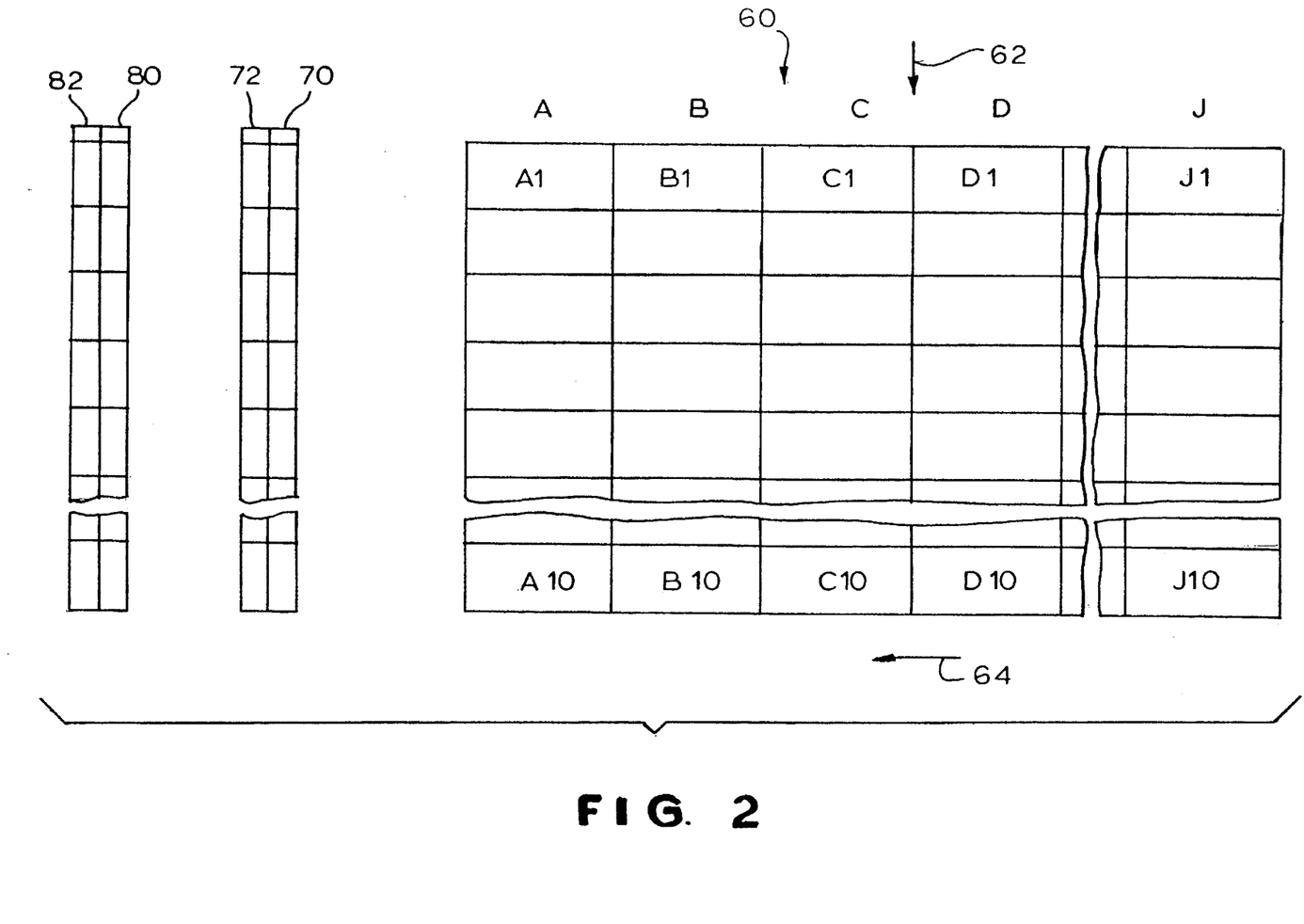
FIG. 2 is a fragmentary schematic representation of alternative apparatus.

Referring now to FIG. 2, the alternative approach separates the time interval spent in assaying each fraction in each detector from the time interval spent in fractionating the effluent. One way to accomplish this involves the use of a two dimensional array of collection devices, generally designated 60, which may be visualized as a series of ten columns labelled A to J, each column having ten rows labelled 1 to 10. The array is used with a device (not shown) that mechanizes the deposition of the fractions with a moving arm dispenser that indexes from one collection device to the next along the same column, in the direction of arrow 62, so that one row 1, 2 . . . 10 after another passes beneath the moving arm. This is combined with a moving table that indexes the entire array at right angles to the movement of the dispenser, in the direction of arrow 64, so that one column A, B . . . J after another passes beneath the dispenser. There are also provided two columns 70, 72 of 10 pretreatment centers each downstream from the initial position of array 60 and two columns 80, 82 of 10 detectors each downstream from pretreatment column 72.

As an example of operation, the first ten fractions 1–10 are deposited in collection devices A1 to A 10 of column A at 20 second intervals. Then the entire array 60 is moved in the direction of arrow 64 so that the collection devices B1 to B10 of column B are under the dispenser and the second ten fractions 11–20 are deposited in collection devices B1 to B10, and so forth until 100 fractions are collected in collection devices A1 to J10. When the array 60 is moved so that the second column B of collection devices is under the dispenser receiving samples 11–20, pretreatment of samples A1 through A10 of column A (now on columns 70) is begun — e.g., evaporation of the samples using heat and streams of nitrogen supplied by a 20 place nitrogen manifold mounted to play on the 20 samples in the two pretreatment columns 70, 72 just past the dispensing column. When the array 60 is moved again, samples 1–10 and 11–20 in columns A and B are evaporated in columns 80 and 82, respectively, while samples 21–30 are being collected in collection devices C1–C10 of column C. Thus, evaporation of the samples in column A is carried out in columns 70 and 72 for the two 200 second intervals available between the two movements of the array (i.e., a 200 sec interval in column 70 during collection of column B and a 200 sec interval in column 72 during collection of column C). When the array 60 is moved again to collect samples 31–40 in collection devices D1–D10 of column D, samples 1–10 in column A are assayed by the 10 detectors in column 80 mounted over rows 1–10. This again is carried out for 20 0 seconds. When the array 60 is moved again, samples 1–10 in column A pass to a second column 82 of 10 detectors, again for 200 seconds, at the same time that samples 11–20 of column B are assayed in the first column 80 of detectors. As before, results are accumulated in electronic memory and calculated so that the assays of individual fractions passing through the different detectors are calculated together.

The precision of the results is the same for passing each sample through 20 detectors for 20 seconds each or through detectors for 200 seconds, since the same number of radioactive events contribute to the measurement. The total time between the emergence of a fraction from the chromatography column and its radioassay is approximately the same. The only slight disadvantages involved are the care required to ensure that each detector produces results equivalent to those of the others and the slightly increased complexity of the fractionation device. The advantages of two dimensional arrays follow from the ability to mount more individual detectors in the same space conveniently. One can envision using 100 or more detectors, arranged in a rectilinear array of 10 rows and even more columns, and a fraction collection array of 10 rows and 30 columns. This fraction collection array would permit a maximum of 300 samples to be collected. However, if fewer fractions are needed, the dispenser can be programmed to deposit fractions only in some of the rows. This diminishes the time each fraction will be assayed since the number of fractions per row determines the time between indexing movements of the array and therefore the time each fraction spends under each detector column.

In addition to the increased versatility, the use of this kind of array simplifies the construction and readout of multiple detector arrays. One can use stationary two-dimensional detectors, as opposed to those using mechanical scanners, such as are used in paper and thin-layer chromatography. These include gas detectors in the Geiger mode that use wires crossing each other at right angles and or scintillation "cameras", both of which record both the occurrence or a radioactive event and its position in two dimensions. Both are more easily applied when the samples are closer to one another.

As with a linear array, chromatographic resolution is determined only by the frequency of fractionation. Sensitivity of detection of properties that require appreciable time for measurement is a function of the total time each fraction spends in detectors.

To summarize, the present invention provides a method which combines high resolution and high sensitivity in an on-line assay of a stream for a property which requires appreciable time for sensitive measurement.

Now that the preferred embodiments of the present invention have been shown and described in detail, various modifications and improvements thereon will become readily apparent to those skilled in the art. Accordingly, the appended claims are to be construed broadly and in a manner consistent with the spirit and scope of the invention described herein.

I claim:

1. A method for the on-line and continuous assay of a stream of changing composition, when both the times and magnitudes of the changes are of interest, for a compound of interest with a property requiring a time within the sensitive volume of a detector sufficient for measurable reaction, comprising the steps of:

(A) dividing the stream at first time intervals predetermined by the requirements for resolution into a plurality of discrete fractions which are prevented from subsequently mixing with each other;

(B) essentially continuously monitoring the stream on line by passing each fraction sequentially through each in a series of at least 10 adjacent detectors sensitive to the specified property so that each fraction spends a predetermined second time interval within the sensitive volume of each detector, is monitored continuously during such predetermined second time interval, and produces signals proportional to the property during such predetermined second time interval; and (C) for each fraction computing the result of the assay by combining the signals from each detector during the predetermined second time interval the fraction is in the detector, taking into consideration the time of arrival of the fraction at the detector and its residence time within it;

the property being measured being one of bioluminescence or chemiluminescence, enzyme activity in an instance where it changes with respect to time, and biologic effect; and the detectors are light detectors when the property is bioluminescence or chemiluminescence, spectrophotometric, colorimetric, fluorometric or electrochemical detectors when the property is enzyme activity, and optical detectors when the property is biologic effect.

2. The method of claim 1 wherein in step (C) the signals produced in each detector during each predetermined second time interval are stored in a memory storage device and the result of the assay of each fraction is continuously calculated, recalculated and optionally displayed using an algorithm which takes into account the signals from successive detectors during the predetermined second time intervals the fraction is in each detector.

3. The method of claim 1 wherein in step (A) the stream is divided at the predetermined first time intervals appropriate to preserve the resolution of the analysis, and in step (B) the property is measured during predetermining second time intervals equal in duration to the predetermined first time intervals.

4. The method of claim 1 wherein the fractions are collected in pockets formed on an elongate strip of film moved stepwise past a source of the stream.

5. The method of claim 4 wherein any solvents in each fraction collected in at least one of said are evaporated to produce a condensed dry fraction prior to passage of the fraction through the first detector in the series.

6. The method of claim 1 wherein the stream is a gas, and each fraction is stripped from the gas stream into a stream of solvent prior to collection.

7. The method of claim 1 wherein the stream is fractionated by segmenting it into a plurality of fractions at predetermined first time interval with immiscible fluid, before causing it to flow into a tubular conduit, the walls of which are not wettable by either the stream or the compound of interest, which process of segmentation prevents the fraction from mixing with each other.

8. The method of claim 7 wherein each fraction is sequentially passed through each detector for an equal predetermined second time interval.

9. The method of claim 8 wherein each equal predetermined second time interval equals in duration the predetermined first time interval.

10. The method of claim 1 wherein each fraction is sequentially passed through each detector for an equal predetermined second time interval.

11. The method of claim 1 wherein the property being measured is bioluminescence or chemiluminescence, and the detectors are light detectors.

12. The method of claim 1 wherein the property being measured is enzyme activity in an instance where it changes with respect to time, the detectors are spectrophotometric, colorimetric, fluorometric or electrochemical detectors and the calculation of the result of the assay is based on the rates of reaction in each detector during each predetermined second time intervals as well as the difference between readings in successive detectors.

13. The method of claim 1 wherein the property being measured is a biologic effect, the detector is optical, and the calculation of the assay is based on differences between readings in successive detectors.

14. The method of claim 1 wherein the stream is the effluent of a chromatography column.

15. The method of claim 1 wherein the stream is the effluent of an electrophoresis column.

16. The method of claim 1 wherein, when a plurality of wavelength measurements are made while a fraction is in each detector, the predetermined second time interval the fraction is in each detector at least 10 seconds per wavelength measurement.

17. The method of claim 12 wherein, when a plurality of wavelength measurements are made while a fraction is in each detector, the predetermined second time interval the fraction is in each detector is at least 10 second per wavelength measurement.

18. The method of claim 4 wherein the stream is a liquid in which the compound of interest is dissolved in a comparatively large volume of more volatile inert solvent, and the compound of interest in each fraction is concentrated by removing the more volatile, inert solvent by evaporation prior to passing the dry fraction through the first detector of the series.

19. The method of claim 1 wherein the stream is a gas and the compound of interest is continuously scrubbed or stripped from the gas into a stream of liquid solvent, followed by collection of fractions of the liquid stream.

20. The method of claim 1 wherein a rate of change determination is made in each detector in the time interval each fraction is in each detector.

21. The method of claim 1 wherein in step (B) each fraction remains in and is continually measured within the sensitive volume of each detector for as much as possible of the time period over which the then currently being taken fraction is collected, so that the time the fraction spends within each detector is maximized, the time the fraction spends between detectors is minimized, and there is no interference with the orderly progression of succeeding fractions through the detection series.

22. The method of claim 1 wherein in step (B) the time spent by each fraction cumulatively between detectors is a fraction of the time spent by each fraction cumulatively within the detectors.

23. The method of claim 1 wherein the computation of the result of the assay is based on the difference between readings in successive detectors and, when applicable, a rate of change determination in each detector during each predetermined second time interval as well.

24. A method for the on-line and continuous assay of a stream of changing composition, when both the times and magnitudes of the changes are of interest, for a compound of interest with a property requiring a time within the sensitive volume of a detector sufficient for measurable reaction, comprising the steps of:

(A) dividing the stream at first time intervals predetermined by the requirements for resolution into a plurality of discrete fractions which are prevented from subsequently mixing with each other;

(B) essentially continuously monitoring the stream on line by passing each fraction sequentially though each in a series of at least 10 adjacent detectors sensitive to the specified property so that each fraction spends a predetermined second time interval within the sensitive volume of each detector, is monitored continuously during such predetermined second time interval, and produces signals proportional to a property during such predetermined second time interval; and (C) for each fraction computing the result of the assay by combining the signals from each detector during the predetermined time interval the fraction is in the detector, taking into consideration the time of arrival of the fraction at the detector and its residence time within it; a rate of change determination in each detector being made in the time interval each fraction is in each detector.

25. A method for on-line and continuous assay of a stream of changing composition, when both the times and magnitudes of the changes are of interest, for a specific property, the measurement of which is enhanced in proportion to the time each portion of the stream remains and is continuously measured within the sensitive volume of a detector, comprising the steps of:

(A) dividing the stream at time intervals into a plurality of fractions great enough in number to achieve the desired resolution of the changes in composition of the stream, each of which fractions is prevented from subsequently mixing with other fractions;

(B) continuously monitoring the stream on-line by passing each fraction sequentially through each in a series of detectors sensitive to the specified property, so that each fraction spends as much of the time interval of collection of subsequent individual fractions within the sensitive volume of each detector in the series being monitored and as little of that time interval being transported between detectors as is mechanically feasible, each fraction being monitored continuously during the time interval it resides in each detector and producing signals proportional to the specified property during that time interval; and (C) for each fraction, computing the result of the assay by combining the signals from each detector during the time interval the fraction is in the detector, taking into consideration the time of arrival of the fraction at the detector and its residence time within it;

the proper being measured being one of bioluminescence or chemiluminescence, enzyme activity in an instance where it changes with respect to time, and biologic effect; and the detectors are light detectors when the property is bioluminescence or chemiluminescence, spectrophoto-metric, colorimetric, fluorometric or electrochemical detectors when the property is enzyme activity, and optical detectors when the property is biologic effect.

26. The method of claim 25 wherein the a rate of change determination in each detector is made in the time interval each fraction is in each detector.

27. A method for on-line and continuous assay of a stream of changing composition, when both the times and magnitudes of the changes are of interest, for a specific property, the measurement of which is enhanced in proportion to the time each portion of the stream remains and is continuously measured within the sensitive volume of a detector, comprising the steps of:

(A) dividing the stream at time intervals into a plurality of fractions teat enough in number to achieve the desired resolution of the changes in composition of the stream, each of which fractions is prevented from subsequently mixing with other fractions;

(B) continuously monitoring the stream on-line by delivering each sequential fraction to an individual detector in an array of a plurality of detectors and monitoring the fraction within that detector for the same number of collection time intervals as there are detectors in the array, following which the fraction is removed and replaced, each fraction being monitored continuously during the time interval it resides in each detector and producing signals proportional to the specified property during that time interval; and (C) for each fraction, computing the result of the assay by combining the signals from each detector during the time interval the fraction is in the detector, taking into consideration the time of arrival of the fraction at the detector and its residence time within it;

the property being measured being one of bioluminescence or chemiluminescence, enzyme activity in an instance where it changes with respect to time, and biologic effect; and the detectors are light detectors when the property is bioluminescence or chemiluminescence, spectrophoto-metric, colorimetric, fluorometric or electrochemical detectors when the property is enzyme activity, and optical detectors when the property is biologic effect.

28. The method of claim 27 wherein a rate of change determination in each detector is made in the time interval each fraction is in each detector.

29. A method for on-line and continuous assay of a stream of changing composition, when both the times and magnitudes of the changes are of interest, for a specific property, the measurement of which is enhanced in proportion to the time each portion of the stream remains and is continuously measured within the sensitive volume of a detector, comprising the steps of:

(A) dividing the stream at time intervals into a plurality of fractions great enough in number to achieve the desired resolution of the changes in composition of the stream, each of which fractions is prevented from subsequently mixing with other fractions;

(B) continuously monitoring the stream on-line by one of series and parallel monitoring procedures;

in the series monitoring procedure, by passing each fraction sequentially through each in a series of detectors sensitive to the specified property, so that each fraction spends as much of the time interval of collection of subsequent individual fractions within the sensitive volume of each detector in the series being monitored and as little of that time interval being transported between detectors as is mechanically feasible, each fraction being monitored continuously during the time interval it resides in each detector and producing signals proportional to the specified property during that time interval;

in the parallel monitoring procedure, by delivering each sequential fraction to an individual detector in an array of a plurality of detectors and monitoring the fraction within that detector for the same number of collection time intervals as there are detectors in the array, following which the fraction is removed and replaced, each fraction being monitored continuously during the time interval it resides in each detector and producing signals proportional to the specified property during that time interval; and (C) for each fraction, computing the result of the assay by combining the signals from each detector during the time interval the fraction is in the detector, taking into consideration the time of arrival of the fraction at the detector and its residence time within it;

the property being measured being one of bioluminescence or chemiluminescence, enzyme activity in an instance where it changes with respect to time, and biologic effect; and the detectors are light detectors when the property is bioluminescence or chemiluminescence, spectro-photo-metric colorimetric, fluorometric or electrochemical detectors when the property is enzyme activity, and optical detectors when the property is biologic effect.

30. The method of claim 29 wherein a rate of change determination in each detector is made in the time interval each fraction is in each detector.

* * * * *